(12) United States Patent
Arakawa et al.

(10) Patent No.: US 8,414,782 B2
(45) Date of Patent: Apr. 9, 2013

(54) PROCESS FOR PRODUCING FLUOROCARBON MICROSTRUCTURE, FLUOROCARBON MICROSTRUCTURE, AND MICROSYSTEM

(75) Inventors: Takahiro Arakawa, Tokyo (JP); Hiroyuki Kusakawa, Tokyo (JP); Shuichi Shoji, Tokyo (JP)

(73) Assignee: Waseda University, Tokyo (JP)

( * ) Notice: Subject to any disclaimer, the term of this patent is extended or adjusted under 35 U.S.C. 154(b) by 0 days.

(21) Appl. No.: 12/522,871

(22) PCT Filed: Jan. 21, 2008

(86) PCT No.: PCT/JP2008/050724
§ 371 (c)(1),
(2), (4) Date: Jan. 27, 2010

(87) PCT Pub. No.: WO2008/088067
PCT Pub. Date: Jul. 24, 2008

(65) Prior Publication Data
US 2010/0167014 A1    Jul. 1, 2010

(30) Foreign Application Priority Data
Jan. 19, 2007    (JP) ................................. 2007-010065

(51) Int. Cl.
C23F 3/00    (2006.01)
B44C 1/22    (2006.01)
(52) U.S. Cl.
USPC .................... 216/11; 216/17; 216/41; 216/83
(58) Field of Classification Search .................... 216/17, 216/41, 83
See application file for complete search history.

(56) References Cited

U.S. PATENT DOCUMENTS

| | | | | |
|---|---|---|---|---|
| 6,790,372 | B2 * | 9/2004 | Roy et al. | 216/10 |
| 7,045,069 | B2 * | 5/2006 | Ozeryansky | 216/11 |
| 2002/0134752 | A1 * | 9/2002 | Kawamura et al. | 216/27 |

FOREIGN PATENT DOCUMENTS

JP    11-121438 A    4/1999

OTHER PUBLICATIONS

A. Milella, F. Palumbo, P. Favia, G. Cicala, and R. d'Agostino, "Deposition mechanism of nanostructured thin films from tetrafluoroethylene glow discharges", Pure and Applied Chemistry, vol. 77, No. 2, pp. 399-414, 2005.*
Milella A. et al., Deposition mechanism of nanostructured thin films from tetrafluoroethylene glow discharges, Pure Appl. Chem., 2005, vol. 77, No. 2, pp. 399-414.

(Continued)

Primary Examiner — Shamim Ahmed
(74) Attorney, Agent, or Firm — McDermott Will & Emery LLP

(57) ABSTRACT

A process for producing a fluorocarbon microstructure capable of easily fabricating a three-dimensional fluorocarbon microstructure. The process for producing a fluorocarbon microstructure comprises a first processing step for forming, on a substrate (2), a film deposition portion with a given pattern made up of a through-hole figure by etching the substrate (2), a fabricating step for forming a fluorocarbon film (6) on an inner circumferential surface of a film deposition portion (9) to fabricate a fluorocarbon region surrounded by the fluorocarbon film (6), and a second processing step for fabricating the fluorocarbon microstructure protruding from a processing surface of the substrate (2) by etching a given region other than a fluorocarbon region on the substrate (2). Hence, the three-dimensional fluorocarbon microstructure can be fabricated which comprises a complicated structure that has conventionally been hard to fabricate. Thus, a microchannel (1) equipped with the three-dimensional fluorocarbon microstructure can be easily fabricated.

5 Claims, 13 Drawing Sheets

OTHER PUBLICATIONS

Lee S. -H et al., Surface Characterization and a Lift-Off Process of Fluorocarbon Thin Film for Micro Protein Patterning, Proceedings of µTAS 2003 7th International COnference on Micro Total Analysis Systems, vol. 2, Oct. 5, 2003, pp. 1093-1096.

* cited by examiner

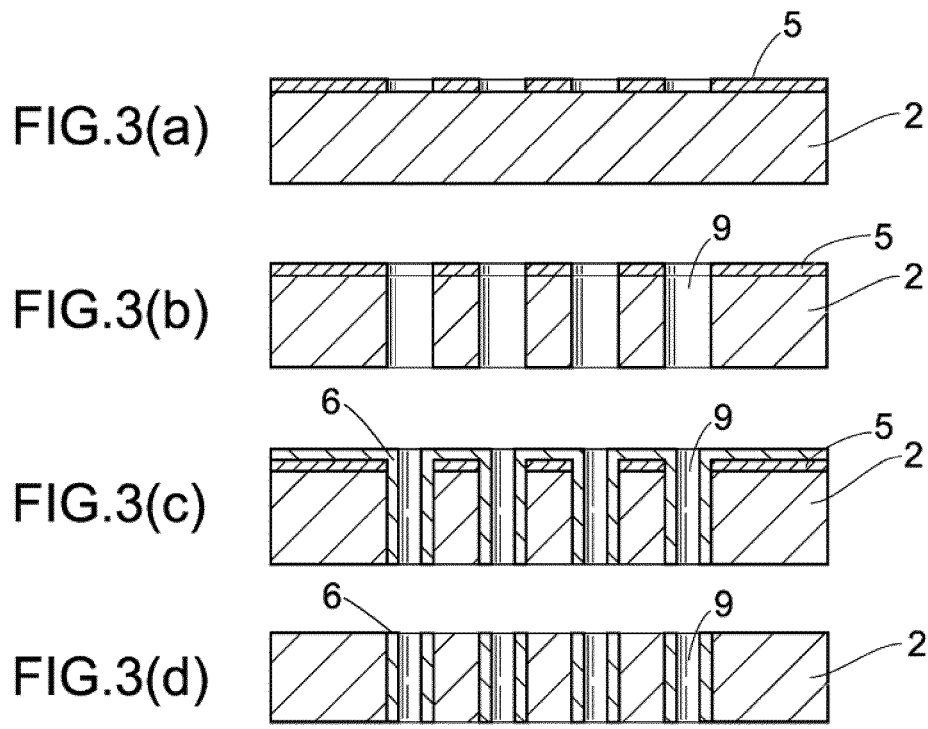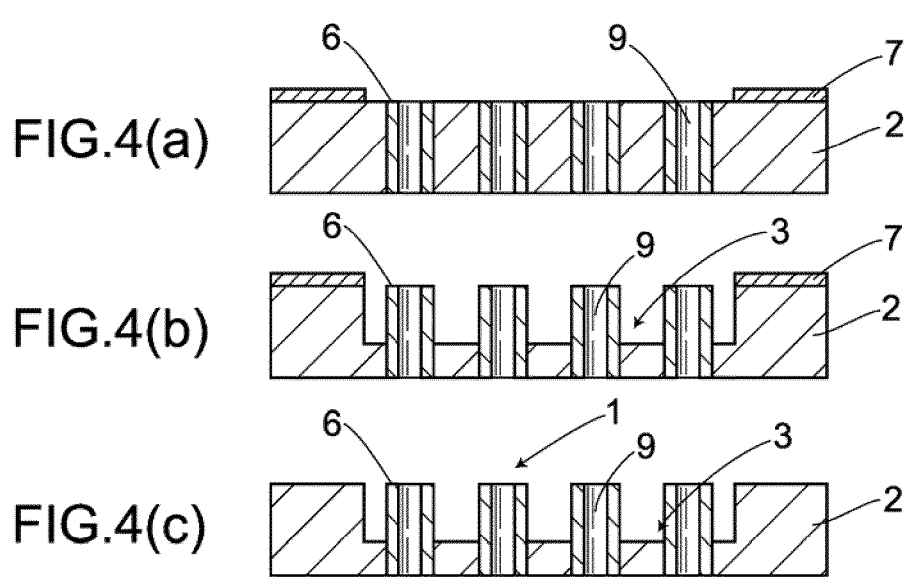

FIG.20
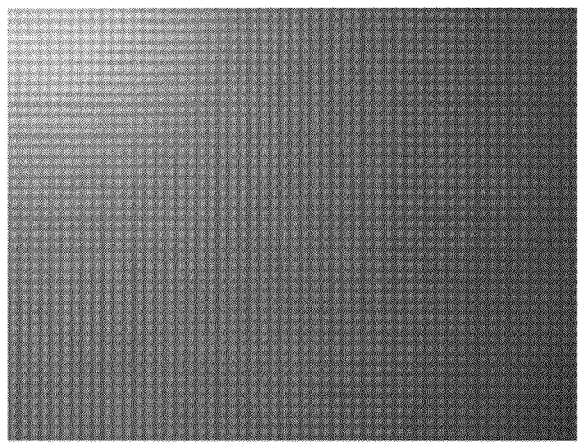
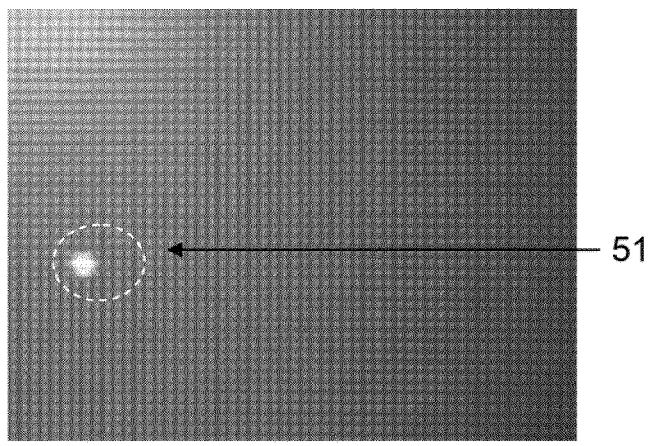
51
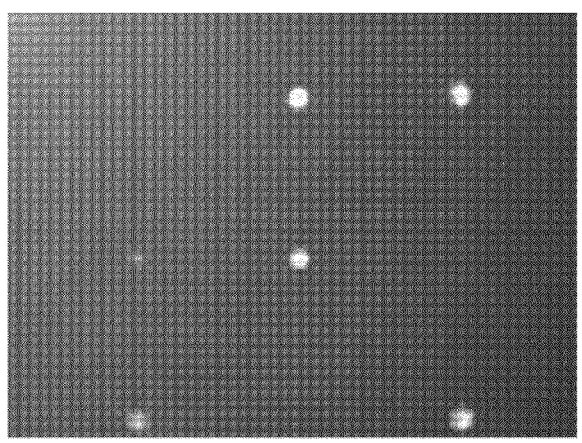

PROCESS FOR PRODUCING FLUOROCARBON MICROSTRUCTURE, FLUOROCARBON MICROSTRUCTURE, AND MICROSYSTEM

CROSS-REFERENCE TO PRIOR APPLICATION

This is the U.S. National Phase Application under 35 U.S.C. §371 of International Patent Application No. PCT/JP2008/050724 filed Jan. 21, 2008, which claims the benefit of Japanese Patent Application No. 2007-010065 filed Jan. 19, 2007, both of which are incorporated by reference herein. The International Application was published in Japanese on Jul. 24, 2008 as WO2008/088067 A1 under PCT Article 21(2).

TECHNICAL FIELD

The present invention relates to a process for producing a fluorocarbon microstructure, a fluorocarbon microstructure and a microsystem.

BACKGROUND ART

Recently, development of microfabrication technology has led to the downsizing of conventional chemical analytical systems, thus resulting in an increased attention being attracted toward the research on a microsystem produced by integrating on a substrate downsized analytical systems for mixing, reaction, separation, detection, and so on. In the microsystem, a fluorocarbon film is employed as a surface protective film of a flow channel because the fluorocarbon film has advantageous features such as excellent chemical resistance and a less adsorptive property for protein. To take the example of one of traditional Microsystems, one of fluorocarbon films such as CYTOP™ (made by Asahi Glass Co., Ltd.) is coated on a PDMS with inferior chemical resistance, thus realizing protection against an organic solvent and reduction in adsorption of fluorescent substance. Further, there is reported a technique in which a fluorocarbon film is patterned on a silicon substrate to fix protein on a specific position.

On the other hand, Japanese unexamined patent application publication No. 11-121438 (Patent document 1) discloses a plasma etching method characterized by a carbon/fluorine ratio of a CF polymer film being 1.1 to 1.8, said CF polymer being deposited on a resist film during an etching process. According to this method, a fluorocarbon film is formed on a substrate plane surface to be used as a protection film.

Patent document 1: Japanese unexamined patent application publication No. 11-121438.

DISCLOSURE OF THE INVENTION

Problem to be Solved by the Invention

According to the conventional arts, however, the use of a fluorocarbon film, having such advantageous features as excellent chemical resistance and less adsorption property for protein, is limited to that as a protective film. Hence, the shape of the fluorocarbon microstructure is restricted by the shape of a member to be protected. As a result, there has been a problem that a three-dimensional fluorocarbon microstructure is difficult to fabricate.

Therefore, with the view of the problems described above, it is an object of the present invention to provide a process for producing a fluorocarbon microstructure by which a three-dimensional fluorocarbon microstructure can be easily fabricated. It is another object of the present invention to provide a three-dimensional fluorocarbon microstructure and a microsystem equipped with such three-dimensional fluorocarbon microstructure.

Mean for Solving the Problem

The present invention has been originated by elaborating an etching processing technology. Then, the present invention is described below.

A first aspect of the present invention is a process for producing a fluorocarbon microstructure comprising a first processing step for forming on a substrate a film deposition portion with a given pattern made up of a depressed figure or a through-hole figure by etching the substrate, a fabricating step for forming a fluorocarbon film on an inner surface of the film deposition portion to fabricate a fluorocarbon region surrounded by the fluorocarbon film, and a second processing step for fabricating a fluorocarbon microstructure protruding from a processing surface of the substrate by etching a given region other than the fluorocarbon region on the substrate.

A second aspect of the present invention is a process for producing a fluorocarbon microstructure in which a resist is patterned on the substrate to etch the substrate in the first processing step; the fluorocarbon film is formed on the inner surface of the film deposition portion and on the resist in the fabricating step; and a removing step is provided in which the resist and the fluorocarbon film on the resist are removed after the fabricating step.

A third aspect of the present invention is a process for producing a fluorocarbon microstructure in which in the second processing step, a resist for the second processing step is patterned on the substrate and then a given region other than the fluorocarbon region on the substrate is etched.

A fourth aspect of the present invention is a process for producing a fluorocarbon microstructure in which a silicon dioxide film is already patterned on the substrate before the second processing step starts and then the substrate is etched with the silicon dioxide film used as a mask in the second processing step.

A fifth aspect of the present invention is a fluorocarbon microstructure in which a fluorocarbon film is formed on an inner surface of a film deposition portion with a given pattern made up of a depressed figure or a through-hole figure formed by etching a substrate; and then by etching a given region other than a fluorocarbon region surrounded by the fluorocarbon film, the fluorocarbon microstructure body is formed which protrudes from a processing surface of the substrate and is surrounded by the fluorocarbon film.

A sixth aspect of the present invention is a microchemical system, including a fluorocarbon microstructure in which a fluorocarbon film is formed on an inner surface of a film deposition portion with a given pattern made up of a depressed figure or a through-hole figure formed by etching a substrate; and then by etching a given region other than a fluorocarbon region surrounded by the fluorocarbon film, the fluorocarbon microstructure body is formed which protrudes from a processing surface of the substrate and is surrounded by the fluorocarbon film.

Effects of the Invention

According to the present invention, the process for producing a fluorocarbon microstructure can be provided which is capable of easily fabricating a three-dimensional fluorocar-

BRIEF DESCRIPTION OF THE DRAWINGS

FIGS. 3 (a), (b), (c) and (d) are cross-sectional views illustrating partial fabricating processes of the microchannel according to the first embodiment of the present invention.

FIGS. 4 (a), (b) and (c) are cross-sectional views illustrating partial fabricating processes of the microchannel according to the first embodiment of the present invention.

FIG. 20 is electron microscope images illustrating the single cell fixing microsystem according to the fourth embodiment of the present invention.

BEST MODE FOR CARRYING OUT THE INVENTION

Hereunder is a description of embodiments of the present invention with reference to the accompanying drawings.

(1) First Embodiment

Figure 1:
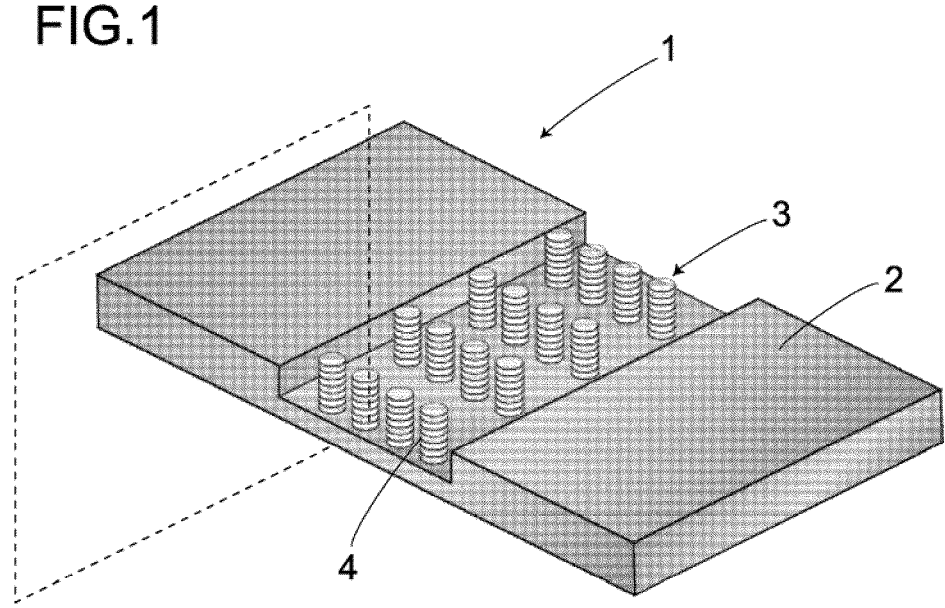
FIG. 1 is an overview illustrating a microchannel according to a first embodiment of the present invention.

FIG. 1 shows an overview of a microchannel, acting as one of microsystems, according to a first embodiment of present invention. In FIG. 1, numeral symbol 1 denotes an entire microchannel according to the first embodiment. The microchannel 1 is provided with a depressed flow channel section 3 formed on one surface of a substrate 2 and a plurality of fluorocarbon microstructures 4 formed on the flow channel section 3. As the substrate 2, if making it possible to process and provide the flow channel section 3 by using various types of microfabrication technologies, any compound semiconductors such as a silicon semiconductor substrate, a GaAs substrate or the like, a semiconductor substrate having an SOI structure, and an insulating substrate may be usable. The substrate is not restricted particularly in size. According to sizes of the flow channel section 3 and a plurality of fluorocarbon microstructures 4, the size of the substrate may be of the order of, e.g., 0.1 μm to 10 mm. Further, the flow channel section 3 is not particularly limited also in width and depth. However, in this case, e.g., the width and the depth are selected as about 200 μm and about 50 to 100 μm, respectively.

Figure 2:
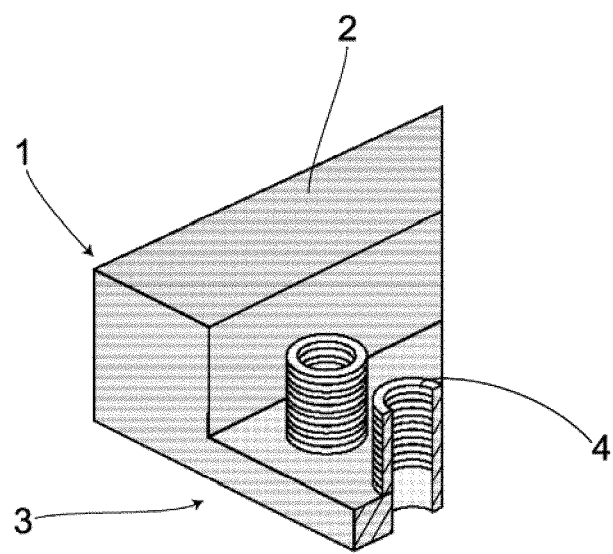
FIG. 2 is a detailed cross-sectional view illustrating an across-sectional structure on a dashed line in FIG. 1.

FIG. 2 is a detailed cross-sectional view showing a cross-sectional structure on the dashed line in FIG. 1. As shown in FIG. 2, in actuality, the fluorocarbon microstructure 4 is arranged on a film deposition portion 9 formed on the substrate 2 and has a tubular three-dimensional structure formed in a tubular manner.

The microchannel 1 described above can be fabricated through the following processes.

An outline of the fabricating processes of the microchannel 1 is shown in FIGS. 3, 4. First, a first processing step is performed to form a through-hole-shaped film deposition portion 9 on the substrate 2. Actually, in this first processing step, a resist 5 is applied to one surface acting as a processing surface of the substrate 2. After having patterned the resist 5 (FIG. 3(a)), the tubular film deposition portion 9 penetrating the substrate 2 is formed by, e.g., a Deep Reactive Ion Etching (Deep-RIE) working process (FIG. 3(b)). Here, the Deep-RIE working process means one of anisotropic etching processes by using dry etching and specifically the process is performed by repeating alternately an $SF_6$ gas etching process and a sidewall protective film forming process by using a $C_4F_8$ gas. In the process, a diameter and depth of the film deposition portion 9 are selected as, e.g., about 30 μm and about 200 μm, respectively.

Next, as shown in FIG. 3(c), a fabricating step is performed to form a fluorocarbon film 6 on an inner circumferential surface of the film deposition portion 9 to fabricate a fluorocarbon region surrounded by the fluorocarbon film 6. Specifically, the process gas of the Deep-RIE working process is changed to perform the process only by using the $C_4F_8$ gas, forming the fluorocarbon film 6 on an inner surface of the film deposition portion 9 and on a surface of the resist 5 (FIG. 3 (c)). Here, the fluorocarbon means a CF-based material represented generally by (?CF2?)n. As raw gases for forming the fluorocarbon film 6 with a CVD method, CxFy-based gases (x, y each denote an integral number) such as $C_2F_4$, $C_2F_6$, $C_3F_8$, $C_4F_8$, $C_5F_8$, $C_6F_6$ can be mentioned. Hydrogen such as $CH_2F_2$, $CHF_3$ or the like may be partially contained in the fluorocarbon film 6 formed. Further, the resist 5 acting as a mask is removed by, e.g., sulfuric acid and a hydrogen peroxide solution. At this time, a fluorocarbon film 6 deposited on the resist 5, together with the resist 5, is removed. As a result, the fluorocarbon film 6 remains over an entire inner surface of the tubular film deposition portion 9, permitting the fluorocarbon region to be formed (FIG. 3(d)).

Finally, a second processing step is performed to fabricate a fluorocarbon microstructure 4 protruding from the processing surface of the substrate 2. Specifically, a resist 7 for the second processing step is applied to the processing surface (i.e., one surface) of the substrate 2 and after the resist 7 has been patterned (FIG. 4(a)), a region other than the fluorocarbon region (a through hole 5) is etched by the Deep-RIE working process to fabricate the flow channel section 3, thereby fabricating a plurality of the fluorocarbon microstructures 4 protruding from the processing surface of the substrate 2 (FIG. 4(b)). Thereafter, by removing the resist 7 for the second processing step, the microchannel 1 can be fabricated which comprises the fluorocarbon microstructures 4 protruding from the processing surface of the substrate 2 (FIG. 4(c)). At this time, the resist 7 for the second processing step is applied to the processing surface of the substrate 2 to be capable of processing the substrate 2 from the processing surface of the substrate 2 or the resist 7 for the second processing step is applied to the other surface of the substrate 2 to be capable of processing the substrate 2 from the other surface of the substrate 2. Further, the fluorocarbon microstructure 4 can be controlled in width by a pattern dimension of the resist 5 in the first processing step or by an etching time of the Deep-RIE working process, while the fluorocarbon microstructure 4 can be controlled in film thickness only by a film forming time of the $C_4F_8$ gas in the fabricating step.

Figure 7:
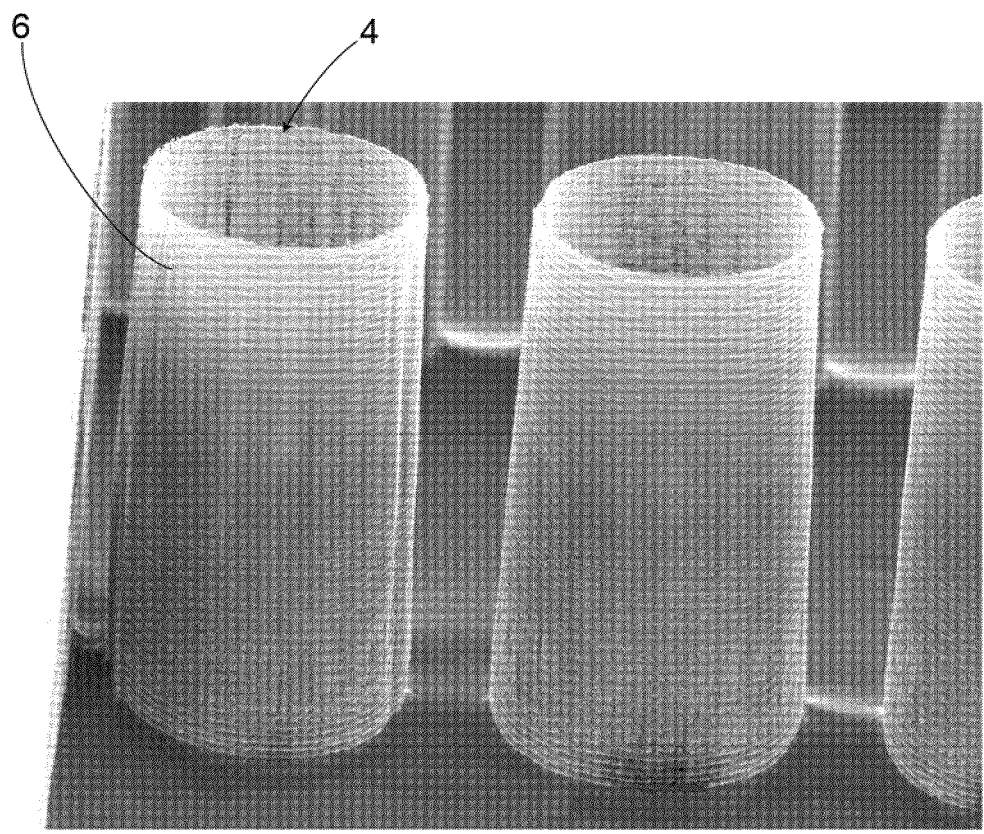
FIG. 7 is an electron microscope image of the microchannel according to the first embodiment of the present invention.

Thus, the fluorocarbon microstructure 4 was fabricated by the processes described above and then its feature was evaluated by using an electron microscope (VE-8000 type made by Keyence Co., Ltd.). FIG. 7 shows the electron microscope photograph. As evidenced by FIG. 7, the fluorocarbon microstructure 4 exhibits a tubular three-dimensional structure and stands 100 μm or so and besides can be found to be very thin in film thickness. Incidentally, an undulate figure which is called scallop and is unique to the result of the Deep-RIE working process can be seen on a surface of the fluorocarbon microstructure 4. In the Deep-RIE working process in FIG. 4(b), it could be verified that on the substrate 2, regions other than the fluorocarbon microstructures 4 were etched in a given depth and only the fluorocarbon microstructure 4 was not etched to remain on the processing surface and thus the fluorocarbon microstructure 4 could be formed in a manner protruding from the flow channel section 3 of the processing surface.

In the microchannel 1 fabricated by the fabricating method mentioned-above, a plurality of the fluorocarbon microstructures 4 having a desired feature can be easily formed in a desired position of the flow channel section 3 while forming the flow channel 3 at a desired position of the processing surface of the substrate 2. Hence, the flow channel section 3 and the fluorocarbon microstructure 4 which have been formed in desired figures and in desired dimensions can be utilized for various applications. Taking an example, when wanting to select only protein with a given size, e.g., given intervals are formed between the fluorocarbon microstructures 4 on the flow channel section 3 and then the protein is made to flow through the flow channels section 3 like this, thereby enabling only the protein capable of passing between the fluorocarbon microstructures 4 to be easily selected. Thus, the application like this is possible.

In the structure set forth above, according to the fluorocarbon microstructure 4 fabricating method in the present embodiment, the method comprises the first processing step for forming on the substrate 2 the film deposition portion 9 with a given pattern made up of the through-hole figure by etching the substrate 2, the fabricating step for forming the fluorocarbon film 6 on the inner circumferential surface of the film deposition portion 9 to fabricate the fluorocarbon region surrounded by the fluorocarbon film 6, and the second processing step for fabricating the fluorocarbon microstructure 4 protruding from the processing surface of the substrate 2 by etching a given region other than the fluorocarbon region on the substrate 2. Hence, the three-dimensional fluorocarbon microstructure 4 can be fabricated which comprises a complicated structure conventionally hard to fabricate and thus, the microchannel 1 equipped with the three-dimensional fluorocarbon microstructure 4 can be easily fabricated.

Further, according to the fluorocarbon microstructure 4 fabricating method in the present embodiment, the resist 5 is patterned on the substrate 2 to etch the substrate 2 in the first processing step and the fluorocarbon film 6 is formed on the inner circumferential surface of the film deposition portion 9 and on the resist 5 in the fabricating step and further the removing step is provided in which the resist 5 is removed after the fabricating step and the fluorocarbon film 6 on the resist 5 is removed as well. Hence, the fluorocarbon film 6 formed on the other portion than the film deposition portion 9 can be easily removed. Thus, the microchannel 1 can be fabricated in which no fluorocarbon film 6 remains in a portion other than fluorocarbon microstructure 4.

Furthermore, according to the fluorocarbon microstructure 4 fabricating method in the present embodiment, in the second processing step, the resist 7 for the second processing step is patterned to etch a given region other than the fluorocarbon region on the substrate 2. Hence, a figure of the given region other than the fluorocarbon region can be determined by patterning the resist 7 for the second processing step after the fabricating step for fabricating the fluorocarbon region. Hence, the microchannel 1 can be fabricated which acts as a microsystem equipped with a microstructure with a large degree of freedom of fabricating processes.

Next, a fabricating process different from that performed for the microchannel 1 set forth above is described below with reference to FIGS. 5, 6 whose corresponding parts to those in FIGS. 3, 4 are attached with the same numerical symbols as those attached in FIGS. 3, 4.

FIGS. 5, 6 show an outline of a modification in the fabricating process of the microchannel 1 in the embodiment described above. In the present modification, a silicon oxide film 10 is formed on both sides of the substrate 2. Before performing a first processing step for forming the through-hole-shaped film deposition portion 9 on the substrate 2, the silicon oxide film 10 is patterned on a region where a flow channel section 3 is to be formed on one side of the substrate 2. Specifically, as shown in FIG. 5(a), a resist 5 is applied to the silicon oxide film 10 formed on one side of the substrate 2. After having patterned the resist 5, the silicon oxide film 10 is etched as shown in FIG. 5(b). For etching the silicon oxide film 10, buffered fluorinated acid (BHF), e.g., is used. After the etching, the resist 5 is removed by using sulfuric acid and a hydrogen peroxide solution. In the same way, the resist (not shown) is applied to the other side opposed to the one side of the substrate 2 and then the silicon oxide film 10 is etched (FIG. 5(c)).

Figure 5A:
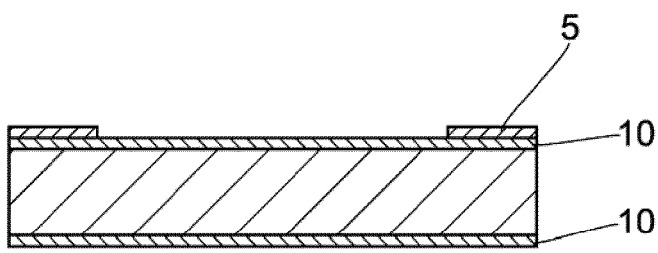
FIGS. 5 (a), (b), (c) and (d) are cross-sectional views illustrating partial fabricating processes of a microchannel according to a modification of the first embodiment of the present invention.
Figure 5B:
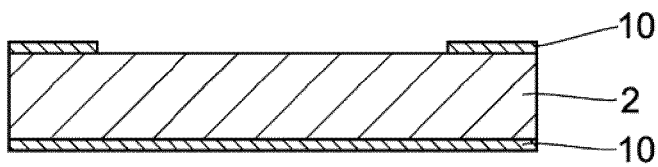
Figure 5C:
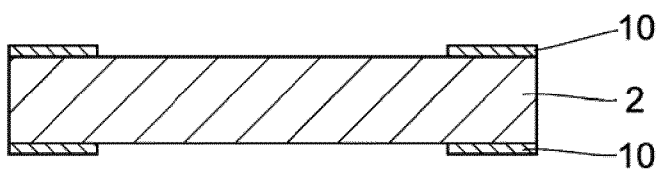
Figure 5D:
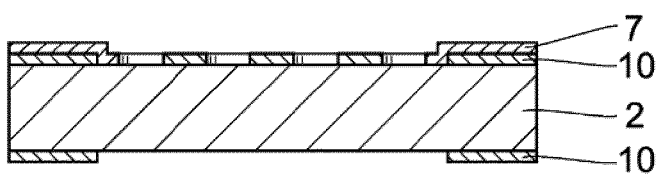
Figure 6A:
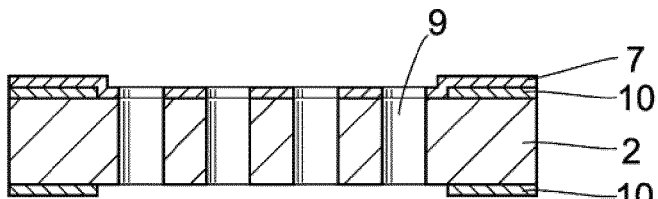
FIG. 6 (a), (b), (c) and (d) are cross-sectional views illustrating partial fabricating processes the microchannel according to the modification of the first embodiment of the present invention.
Figure 6B:
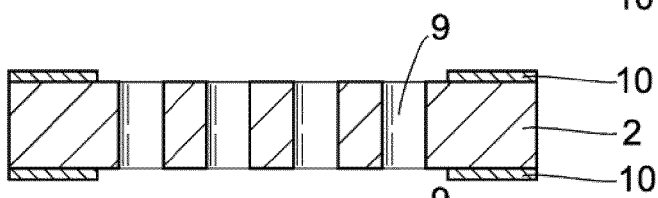
Figure 6C:
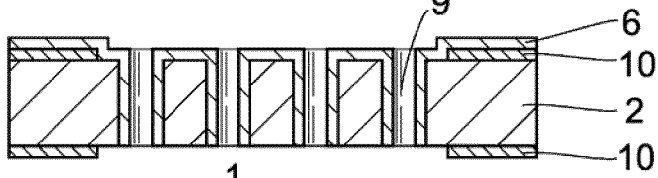
Figure 6D:
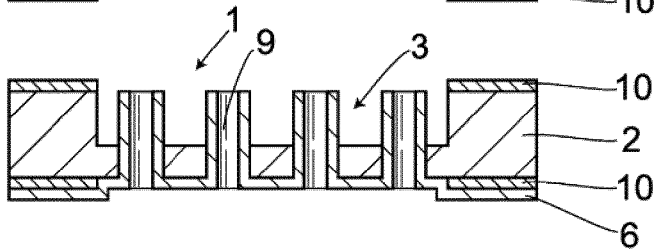

Then, the first processing step is performed to form the through-hole-shaped film deposition portion 9 on the substrate 2. In the first processing step of the present modification, the resist 7 is again applied to the surface of the substrate 2 and after having patterned the resist 7 as shown in FIG. 5(d), the through-hole-shaped film deposition portion 9 is formed by, e.g., the Deep-RIE working process as shown in FIG. 6(a). After having formed the through-hole-shaped film deposition portion 9 by the Deep-RIE working process, the resist 7 is removed by sulfuric acid and a hydrogen peroxide solution (FIG. 6(b)). At this time, a diameter and a depth of the film deposition portion 9 are, e.g., of the order of 30 μm and 200 μm, respectively.

Next, a fabricating step is performed to fabricate the fluorocarbon region surrounded by a fluorocarbon film 6 in an inner circumferential surface of the film deposition portion 9. Specifically, the Deep-RIE working process is performed only by using the $C_4F_8$ gas, thus forming the fluorocarbon film 6 on the inner circumferential surface of the film deposition portion 9, a surface of the substrate 2 and a surface of the silicon oxide film 10.

Finally, the second processing step is performed to fabricate the fluorocarbon microstructure 4 protruding from the other surface acting as a processing surface of the substrate 2. Specifically, the flow channel section 3 is fabricated from the other surface of the substrate 2 by etching a given region other than the fluorocarbon region with the oxide silicon film 10 used as a mask. As a result, a plurality of the fluorocarbon microstructures 4 protruding from the other surface of the substrate 2 is fabricated (FIG. 6(d)). Thus, the microsystem comprising the substrate 2 and the fluorocarbon microstructure 4 protruding from the processing surface of the substrate 2 can be fabricated also by the fabricating method like this. At this time, the fluorocarbon microstructure 4 can be controlled in width by a pattern dimension of the resist 7 in the first processing step or by an etching time in the Deep-RIE working process, while of the fluorocarbon microstructure 4 body can be controlled in film thickness only by the film forming time of the $C_4F_8$ gas in the fabricating step.

In the above structure, according to the fluorocarbon microstructure 4 fabricating method in the present modification, the method comprises the first processing step for forming on the substrate 2 the film deposition portion 9 with a given pattern made up of the through-hole figure by etching the substrate 2, the fabricating step for forming the fluorocarbon film 6 on the inner circumferential surface of the film deposition portion 9 to fabricate the fluorocarbon region surrounded by the fluorocarbon film 6, and the second processing step for fabricating the fluorocarbon microstructure 4 protruding from the processing surface of the substrate 2 by etching a given region other than the fluorocarbon region surrounded by the fluorocarbon film 6. Hence, the three-dimensional fluorocarbon microstructure 4 can be fabricated which comprises a complicated structure conventionally hard to fabricate. Thus, the microchannel 1 equipped with the three-dimensional fluorocarbon microstructure 4 can be easily fabricated.

Further, according to the fluorocarbon microstructure 4 fabricating method in the present modification, the silicon oxide film has been patterned on the other surface (that is, a processing surface) of the substrate 2 before the second processing step starts and the substrate 2 is etched with the silicon oxide film used as a mask in the second processing step. Therefore, processes of newly applying a resist and patterning become unnecessary. Hence, the microchannel 1 equipped with the three-dimensional fluorocarbon microstructure can be fabricated through simpler processes as compared with those in the above first embodiment.

(2) Second Embodiment

Figure 9A:
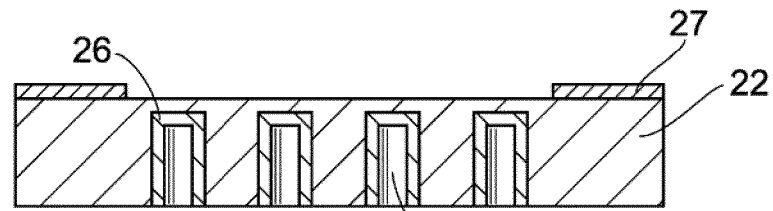
FIGS. 9 (a), (b) and (c) are cross-sectional views illustrating partial fabricating processes of the microchannel according to the second embodiment of the present invention.
Figure 9B:
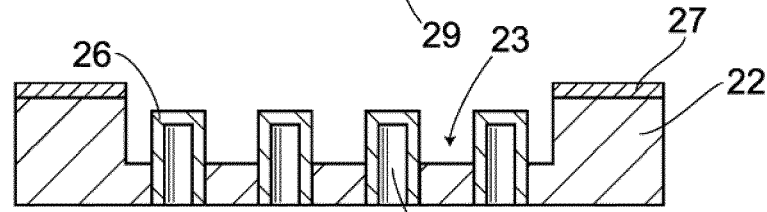
Figure 9C:
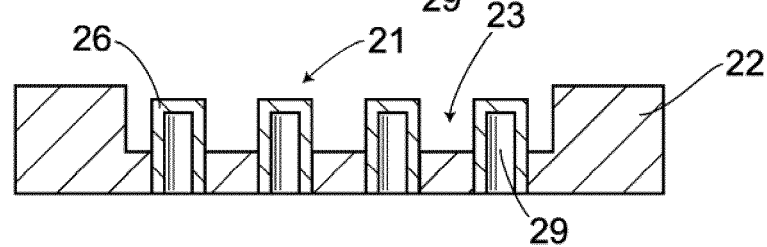

FIG. 9(c) shows a microchannel 21 according to a second embodiment. This microchannel 21 is different from the microchannel 1 according to the above first embodiment only in a figure of the fluorocarbon microstructure 4. In actuality, the fluorocarbon microstructure 4 is formed on a flow channel section 23 of a substrate 22 and has a tubular three-dimensional structure whose upper opening of its tubular portion is closed with a ceiling.

The above microchannel 21 acting as a microsystem can be fabricated by the following processes.

FIGS. 8, 9 show an outline of fabricating processes of the microchannel 21. First, a first processing step is performed to form a depressed film deposition portion 29 on the substrate 22. In actuality, in the first processing step, a resist 25 is applied to one surface of the substrate 22 and after having patterned the resist 25 as shown in FIG. 8(a), the depressed film deposition portion 29 is formed by, e.g., the Deep-RIE working process described above on the substrate 22 (FIG. 8(b)). In actuality, the film deposition portion 29 does not penetrate the substrate 22 and is etched into a given depth to thereby be formed in a bottomed and tubular figure. In addition, in the present embodiment, a diameter and depth of the film deposition portion 29 are selected on the order of, e.g., 30 μm and on the order of, e.g., 150 μm, respectively.

Figure 8A:
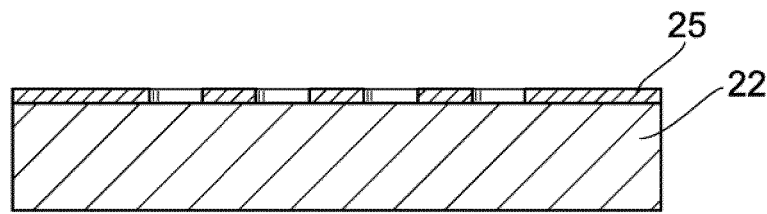
FIGS. 8 (a), (b), (c) and (d) are cross-sectional views illustrating partial fabricating processes of a microchannel according to a second embodiment of the present invention.
Figure 8B:
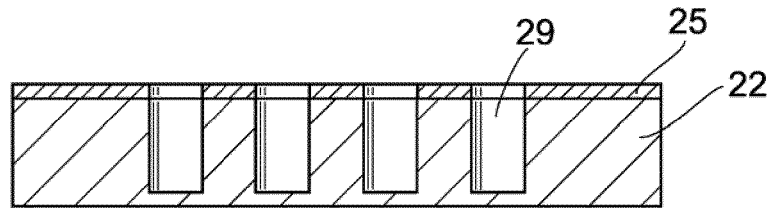
Figure 8C:
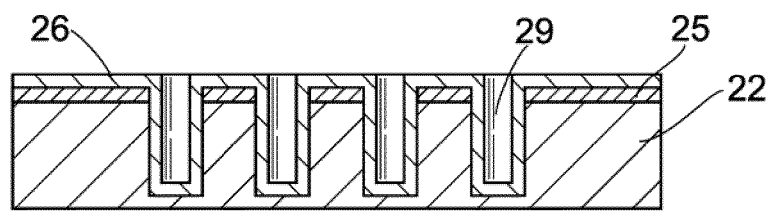
Figure 8D:
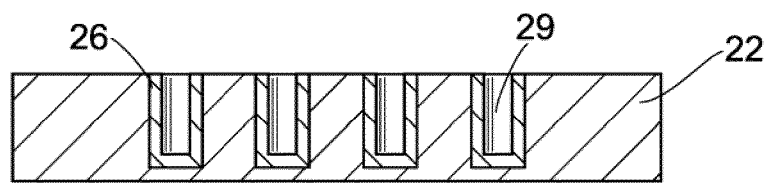

Next, as shown in FIG. 8(c), the fabricating step is performed to fabricate the fluorocarbon region surrounded by the fluorocarbon film 26 is fabricated on an inner circumferential surface and bottom surface of the film deposition portion 29. Specifically, changing a processing gas of the Deep-RIE working, the processing is performed only by the $C_4F_8$ gas, forming a fluorocarbon film 26 on the inner circumferential surface and bottom surface of the film deposition portion 29 and a surface of the resist 25 (FIG. 8(c)). Further, the resist 25 acting as a mask is removed by, e.g., sulfuric acid and a hydrogen peroxide solution. At this time, the fluorocarbon film 26 deposited on the resist 25, together with the resists 25, is removed. Here, in the second embodiment, the film deposition portion 29 has been formed in the bottomed tubular figure and thereby the fluorocarbon film 26 remains only on the entire inner circumferential surface and entire bottom surface of the film deposition portion 29. Hence, the bottomed fluorocarbon region can be formed (FIG. 8(d)).

Figure 19A:
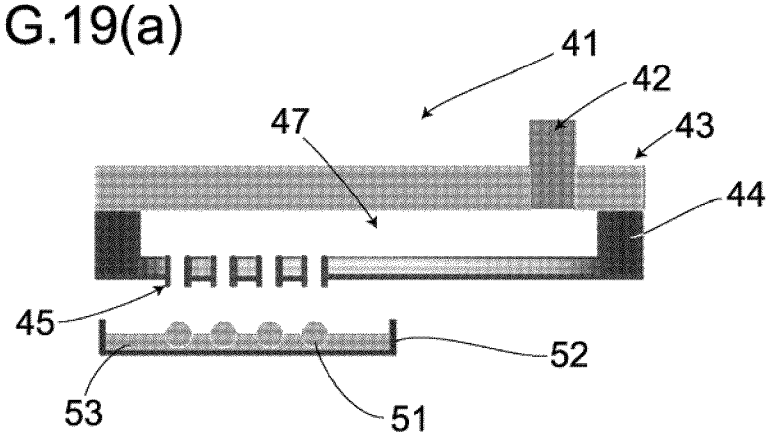
FIGS. 19 (a), (b) and (c) are cross-sectional views illustrating the single cell fixing microsystem according to the fourth embodiment of the present invention.
Figure 19B:
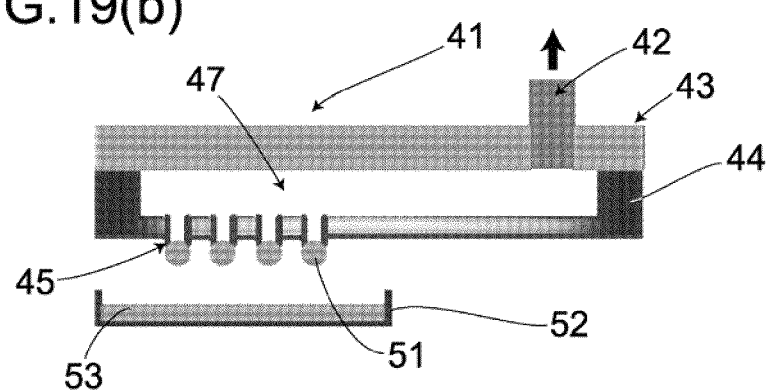
Figure 19C:
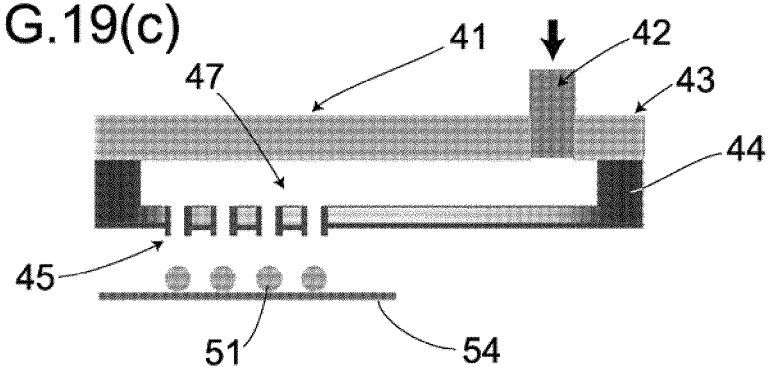

Finally, the second processing step is performed to fabricate the fluorocarbon microstructure 4 protruding from the other surface acting as a processing surface of the substrate 22. Specifically, a resist 27 for the second processing step is applied to the other surface of the substrate 22 and after having patterned the resist 27 for the second processing step as shown in FIG. 9(a), a region other than the fluorocarbon region is etched on the other surface of the substrate 22 by the Deep-RIE working process and thereby the flow channel 23 is made up, thus fabricating a plurality of the fluorocarbon microstructures 4 protruding from the other surface of the substrate 22 (FIG. 9(b)). Thus, in the second embodiment, a tubular three-dimensional fluorocarbon microstructure 4 whose tubular upper opening is closed with a ceiling based on a figure of the film deposition portion 29 can be fabricated on the processing surface of the substrate 22. Afterward, by removing the resist 27 for the second processing step, the microchannel 21 can be fabricated which comprises the substrate 22 and the fluorocarbon microstructure 4 which protrudes from the processing surface of the substrate 22 and has the ceiling (FIG. 19(c)). At this time, the resist 27 for the second processing step can be applied to the processing surface of the substrate 22 to enable the substrate 22 to be processed from the processing surface or the resist 27 for the second processing step can be applied to the other surface of the substrate 22 to enable the substrate 22 to be processed from the other surface. Further, the fluorocarbon microstructure 4 can be controlled in width by a pattern dimension of the resist 25 for the first processing step or by an etching time in the Deep-RIE working process, while the fluorocarbon microstructure 4 can be controlled in film thickness only by the film forming time of the $C_4F_8$ gas in the fabricating step.

In addition, according to the microchannel 21 fabricated by the fabricating method described above, in the same way as in the first embodiment, for example, such an application is possible that when wanting to select only protein with a given size, intervals between the fluorocarbon microstructures 4 on the flow channel section 23 have been formed in a given dimension and then the protein is allowed to flow into the flow channel section 23 and thereby only the protein capable of passing between the fluorocarbon microstructures 4 can be easily selected. In this case, the protein or the like can be prevented from accidentally entering hollow portions inside the tubular portions since an upper extremity of the tubular portion in the fluorocarbon microstructure 4 is closed with the ceiling.

In the structure described above, according to the fluorocarbon microstructure 4 fabricating method in the present embodiment, the method is equipped with the first processing step in which the film deposition portion 29 with a given pattern made up of a depressed figure is formed on the substrate 22 by etching the substrate 22, the fabricating step for forming the fluorocarbon film 26 on an inner surface of the film deposition portion 29 to fabricate the fluorocarbon region surrounded by the fluorocarbon film 26, and the second processing step for fabricating the fluorocarbon microstructure 4 protruding from the processing surface of the substrate 22 by etching a given region other than the fluorocarbon region on the substrate 22. Hence, the three-dimensional fluorocarbon microstructure 4 can be fabricated which comprises a complex structure conventionally hard to fabricate and thus the microchannel 21 can be easily fabricated which is equipped with the three-dimensional fluorocarbon microstructure 4.

Further, according to the fluorocarbon microstructure 4 fabricating method in the present embodiment, the resist 25 is patterned on the substrate 22 to etch the substrate 22 in the first processing step, the fluorocarbon film 26 is formed on the inner surface of the film deposition portion and on the resist 25 and further the removing step is provided in which the resist 25 after the fabricating step is removed and the fluorocarbon film 26 on the resist 25 is removed as well. Hence, the fluorocarbon film 26 is easily removed which has been formed on the portion other than the film deposition portion 29. Thus, the microchannel 21 can be easily fabricated in which the fluorocarbon film 26 does not remain on a portion other than the fluorocarbon microstructure 4.

Furthermore, according to the microstructure 4 fabricating method in the present embodiment, the resist 27 for the second processing step is patterned on the substrate 22 in the second processing step and then a given region other than the fluorocarbon region on the substrate 22 is etched. Hence, after the fabricating step for fabricating the fluorocarbon region, a figure of the given region other than the fluorocarbon region can be determined by the patterning of the resist 27 for the second processing step, thus being capable of fabricating a microchannel 21 acting as a microsystem equipped with a microstructure with a large degree of freedom of fabricating processes.

Next, the following is a description of a modified fabricating process different from the fabricating process of the flow channel 21 described above with reference to FIGS. 10, 11 whose corresponding parts to those in FIGS. 8, 9 are attached with the same numerical symbols as those attached in FIGS. 8, 9.

FIGS. 10, 11 show an outline of a modification in the fabricating process of the microchannel 21 described above, In the present modification, a silicon oxide film 20 is formed on both surfaces of the substrate 22. Before a first processing first step is performed to form a depressed film deposition potion 29 on a substrate 22, the silicon oxide film 20 is patterned in a region where a flow channel section 23 is formed on one surface of the substrate 22. Specifically, as shown in FIG. 10(a), the resist 25 is applied to an upper portion of the silicon oxide film 20 formed on the one surface of the substrate 22 and after having patterned the resist 25, the silicon oxide film 20 is etched as shown in FIG. 10(b). The silicon oxide film 20 is etched by using, e.g., buffered hydrogen fluoride (BHF) and after the etching, the resist 25 is removed by sulfuric acid and a hydrogen peroxide solution. Similarly, the resist (not shown) is applied also to the other surface opposed to the one surface of the substrate 22 to etch the silicon oxide film 20 (FIG. 10(c)).

Figure 10A:
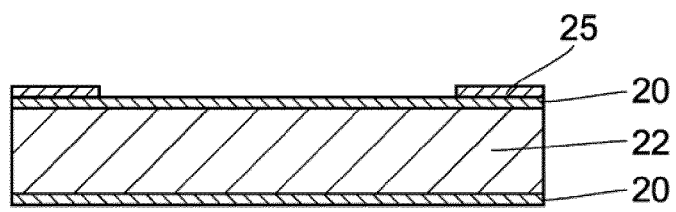
FIGS. 10 (a), (b), (c) and (d) are cross-sectional views illustrating partial fabricating processes of the microchannel according to a modification of the second embodiment of the present invention.
Figure 10B:
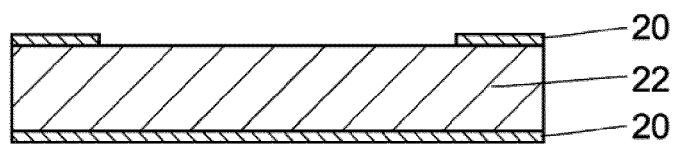
Figure 10C:
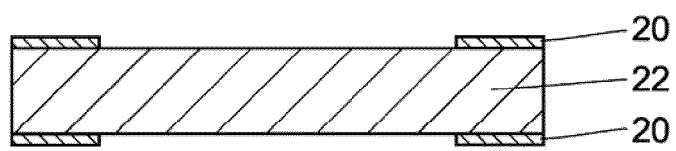
Figure 10D:
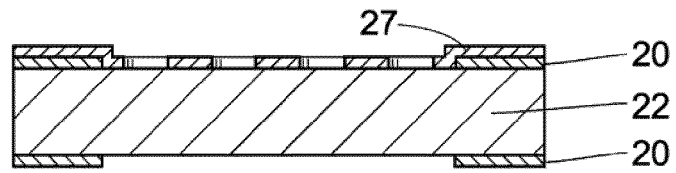
Figure 11A:
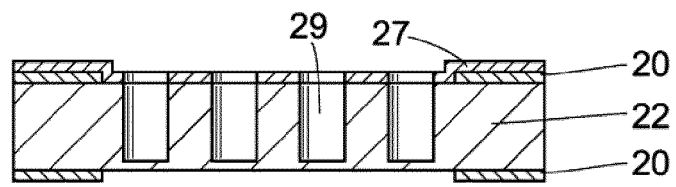
FIGS. 11 (a), (b), (c) and (d) are cross-sectional views illustrating partial fabricating processes of the microchannel according to the modification of the second embodiment of the present invention.
Figure 11B:
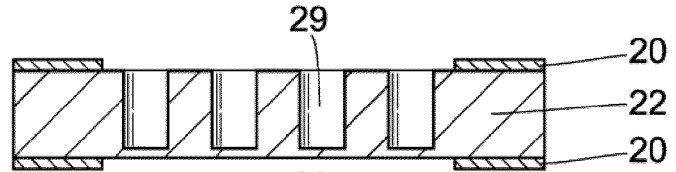
Figure 11C:
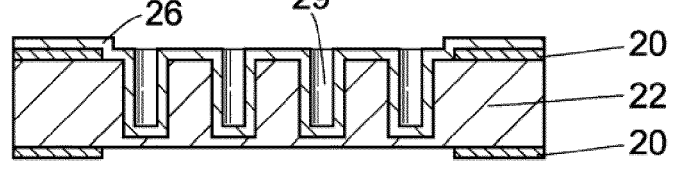
Figure 11D:
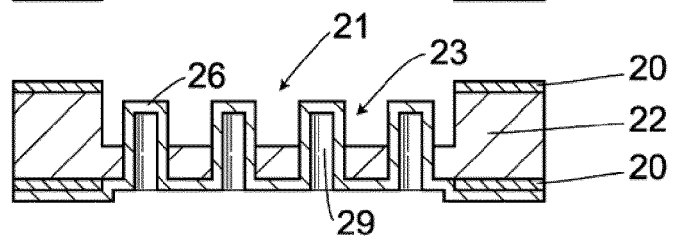
Figure 12:
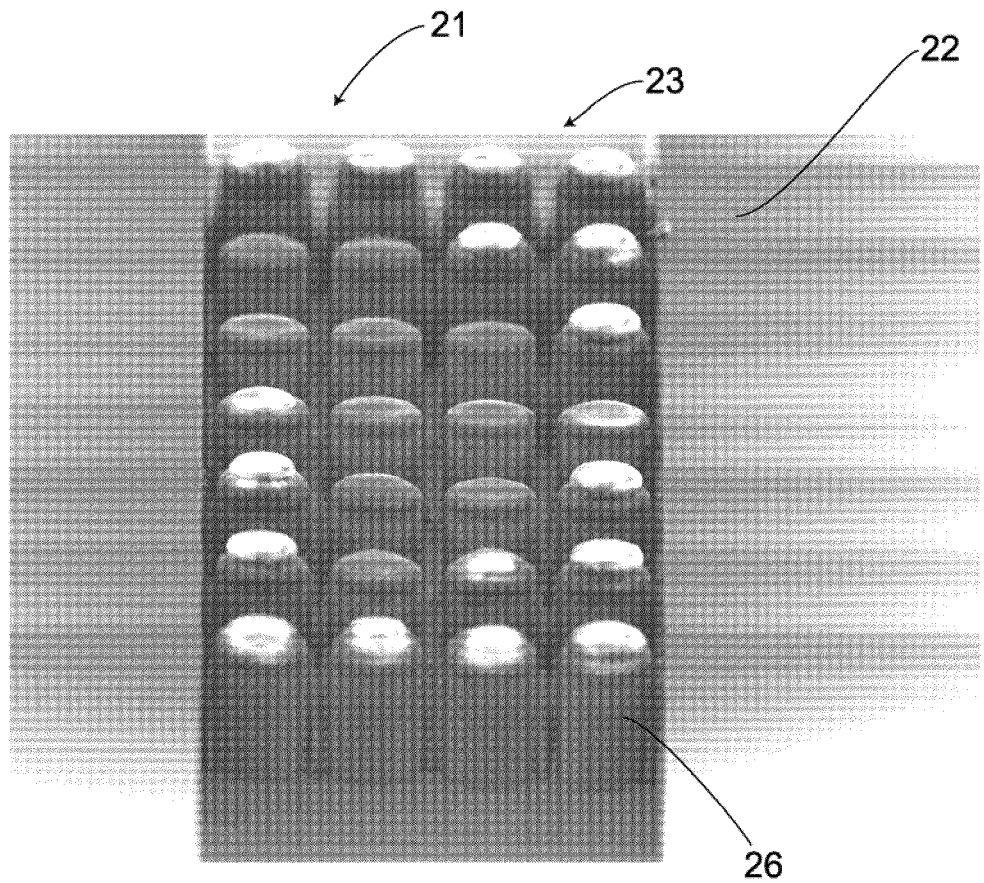
FIG. 12 is an electron microscope image of the microchannel according to the second embodiment of the present invention.

Next, a first processing step is performed to form the depressed film deposition portion 29 on the substrate 22. In the first processing step in the present modification, the resist 27 is again applied to the surface of the substrate 22 and after having patterned the resist 27 as shown in FIG. 10(d), a bottomed and depressed film deposition portion 29 is formed by, e.g., the Deep-RIE working process as shown in FIG. 11(a). After having formed the film deposition portion 29 by the Deep-RIE working process, the resist 27 is removed by sulfuric acid and a hydrogen peroxide solution (FIG. 11(b)). At this time, a diameter and depth of the film deposition portion 29 are selected as on the order of 30 μm and on the order of 200 μm, respectively.

Then, a fabricating step is performed to fabricate a fluorocarbon region surrounded by a fluorocarbon film 26 on an inner circumferential surface and bottom surface of the film deposition portion 29. Specifically, the Deep-RIE working process is performed only by the $C_4F_8$ gas, thus forming the fluorocarbon film 26 on the inner circumferential surface and bottom surface of the film deposition portion 29, a surface of the substrate 22, and a surface of the silicon oxide film 20.

Finally, a second processing step is performed to fabricate the fluorocarbon microstructure 4 protruding from the other surface acting as a processing surface of the substrate 22. Specifically, a given region other than the fluorocarbon region is etched from the other surface of the substrate 22 by the Deep-RIE working process with the silicon oxide film 20 used as a mask and thereby a flow channel section 23 is fabricated. As a result, a plurality of fluorocarbon microstructures 4 can be fabricated which protrudes from the other surface of the substrate 22 and has a ceiling (FIG. 11(d)). Thus, even by the fabricating method like this, a microsystem can be fabricated which comprises the substrate 22 and the depressed fluorocarbon microstructures 4 protruding from the processing surface of the substrate 22. At this time, the fluorocarbon microstructure 4 can be controlled in width by a pattern dimension of the resist 27 for the first processing step or the etching time in the Deep-RIE working process, while the fluorocarbon microstructure 4 can be controlled in film thickness only by a film forming time of the $C_4F_8$ gas in the fabricating step.

In the structure described above, according to the modified fluorocarbon microstructure 4 fabricating method, the method comprises the first processing step for forming the film deposition portion 29 with a given pattern made up of a depressed figure on the substrate 22 by etching the substrate 22, the fabricating step for forming the fluorocarbon film 26 on the inner circumferential surface of the film deposition portion 29 to fabricate the fluorocarbon region surrounded by the fluorocarbon film 26, and the second processing step for fabricating the fluorocarbon microstructure 4 protruding from the processing surface of the substrate 22 by etching a given region other than the fluorocarbon region on the substrate 22. Hence, the three-dimensional fluorocarbon microstructure 4 can be fabricated which comprises a complicated structure conventionally hard to fabricate. Thus, the microchannel 21 can be easily fabricated which is equipped with the three-dimensional fluorocarbon microstructure 4.

Further, according to the fluorocarbon microstructure 4 fabricating method in the present embodiment, the silicon oxide film has been patterned on the other surface (that is, a surface to be processed) of the substrate 22 before the second processing step starts and in the second processing step, the substrate is etched with the silicon oxide film used as a mask. Therefore, processes of newly applying a resist and patterning become unnecessary. Hence, the microchannel 21 equipped with the three-dimensional fluorocarbon microstructure can be fabricated with simpler processes as compared with the above second embodiment.

(3) Third Embodiment

Figure 13:
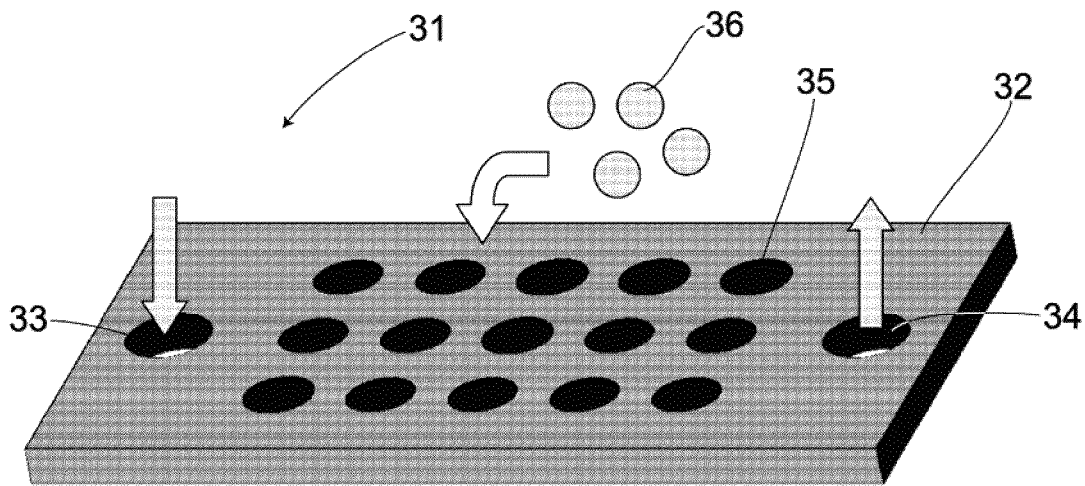
FIG. 13 is an overview illustrating a cell culture system according to a third embodiment of the present invention.
Figure 14A:
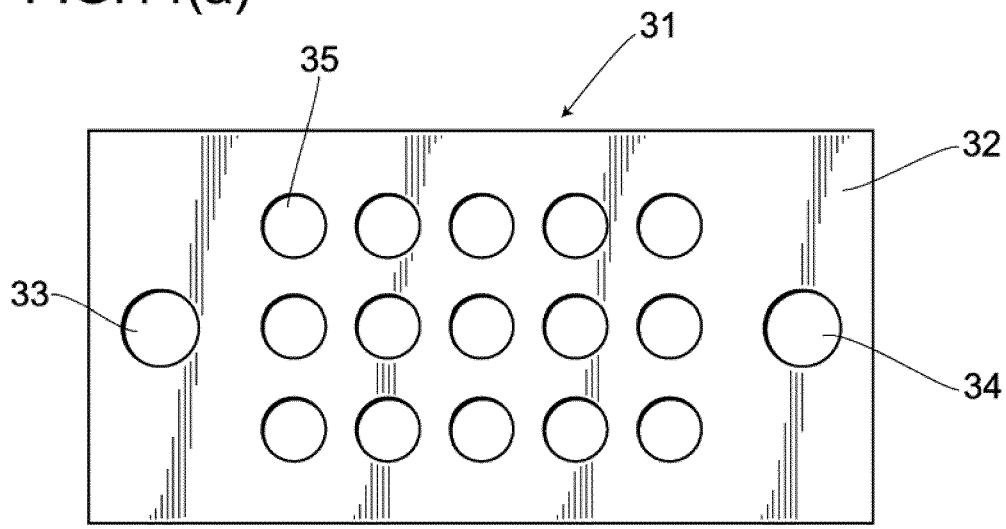
FIGS. 14 (a) and (b) are upper and lower views illustrating the cell culture system according to the third embodiment of the present invention.
Figure 14B:
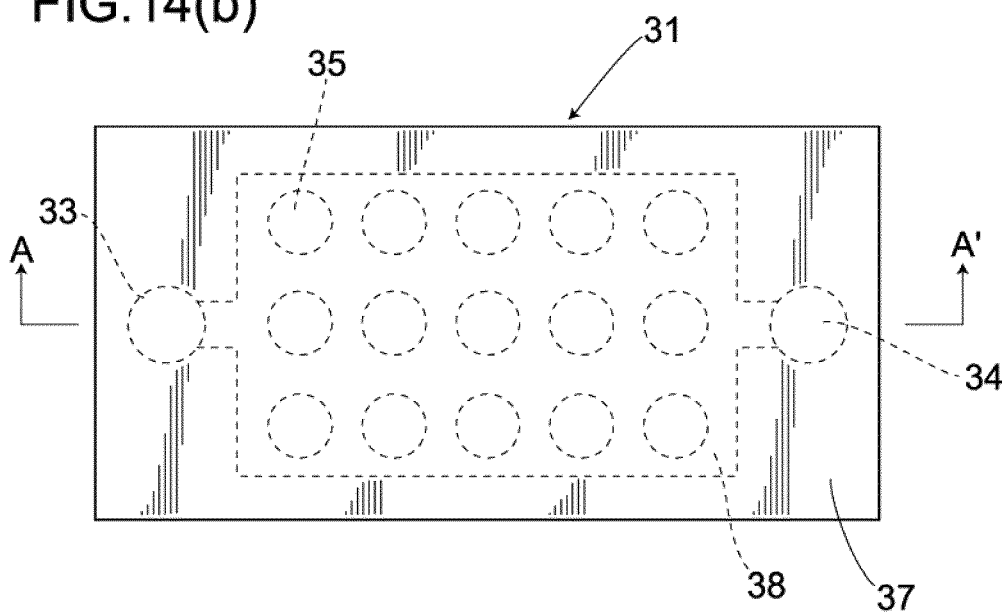
Figure 15:
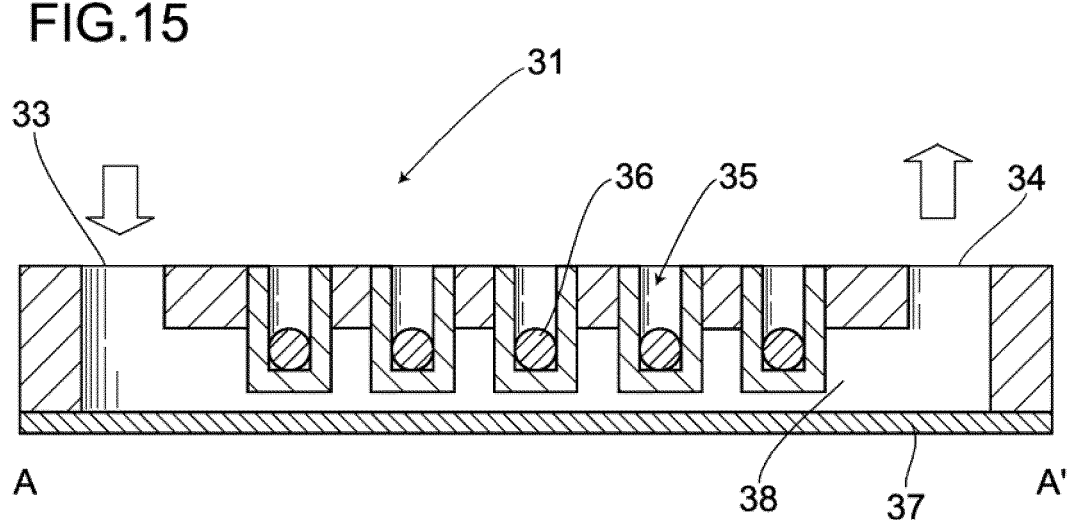
FIG. 15 is a cross-sectional view illustrating the cell culture system according to the third embodiment of the present invention.

In FIG. 13, an overview of a cell culture well is shown which acts as a microsystem according to a third embodiment of the present invention. In FIG. 13, numeral symbol 31 denotes the whole of the cell culture well according to the third embodiment. The cell culture well 31 includes a cell culture medium inlet 33 formed on one surface of the substrate 32, a cell culture section 35 that is a fluorocarbon microstructure, and a cell culture medium outlet 34.

The cell culture well 31 as set forth above is fabricated with the following processes. After having fabricated a flow channel section 38 in the cell culture well 31, Pyrex (trademark registration) 37, e.g., is bonded to one surface of the substrate 32. At this time, the modified microstructure described above can be employed for the cell culture well 31. Further, a microchannel for introducing cells can be separately provided.

The cell culture well 31 thus structured can be used as described below

First, a cell 36 intended to be cultured is housed from above into the cell culture section 35 by using a micro pipette or the like. The cell culture medium is introduced from the cell culture medium inlet 33. After having flowed through the flow channel section 38 in such a manner as to immerse the cell culture section 35, the cell culture medium is discharged from the cell culture medium outlet 34. When the cell culture well 31 is thus utilized, the cell culture medium is diffused into the cell culture section 35 due to the net-like configuration of the bottomed tubular cell culture section 35, thereby providing the potential for proposing a new cell culture method. Further, it is possible to control cell culture by regulating a cell culture medium flow to a target cell.

Figure 16:
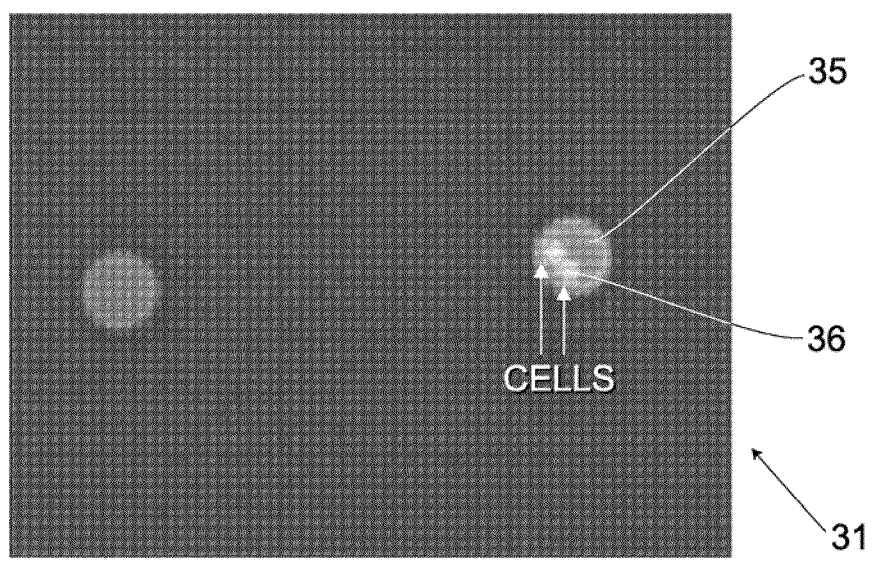
FIG. 16 is an electron microscope image of the cell culture system according to the third embodiment of the present invention.

In FIG. 16, a fluorescent microscope image is shown when the cell 36 has been introduced into the cell culture well 31. As the cell 36, the NIH3T3 (Mouth embryonic fibroblast cell line) (a cultured cell separated from a fetal skin of a mouth) was employed. It was verified from FIG. 16 that even if the cell culture medium was allowed to flow, the cell was held inside the cell culture section 35. Further, it was learned that the cell culture section 35 was excellent in endurance as the film structure was not damaged even after the cell culture medium had been allowed to flow. So, the number of the cells 36 which can be introduced into the cell culture section 35 can be controlled by regulating a diameter of the culture section 35 in the cell culture well 31.

(4) Fourth Embodiment

Figure 17:
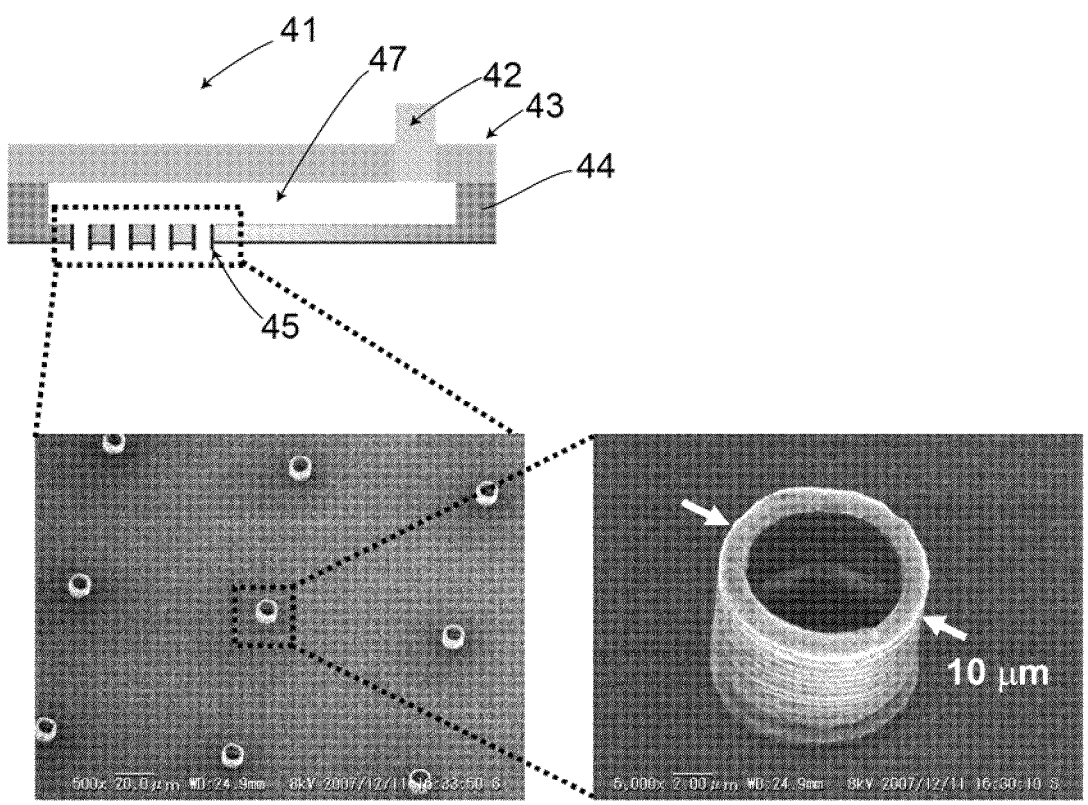
FIG. 17 is overviews illustrating a single cell fixing microsystem according to a fourth embodiment of the present invention.

FIG. 17 shows an overview of a single cell fixing microsystem 41 acting as a microsystem according to a fourth embodiment of the present invention, together with an electron microscope image of a fluorocarbon microstructure 45. In FIG. 17, the single cell fixing microsystem 41 acting as a microsystem is provided with a depressed flow channel section 47 formed on one surface of the substrate 44, a lid 43 arranged on the flow channel section 47 to be used for the flow channel, a suction hole 42 provided in the lid 43 to suck a gas, and a plurality of fluorocarbon microstructures 45 formed underneath the flow channel section 47. In the present embodiment, the plurality of the fluorocarbon microstructures 45 functions as cell fixing protrusions.

The above single cell fixing microsystem 41 acting as a microsystem is fabricated through the following processes.

FIG. 18 shows an outline of fabricating processes of the single cell fixing microsystem 41. First, the substrate 2 is etched to form the flow channel section 47 on a substrate 2 (FIG. 18(a)). Then, as a first processing step, a resist 5 is applied to one surface acting as a processing surface of the substrate 2 and after having patterned the resist 5, a tubular film deposition portion 9 penetrating the substrate 2 is formed by e.g., the Deep-RIE working process (FIG. 18(b)).

Next, a fabricating step is performed to form a fluorocarbon film 6 in an inner circumferential surface of the film deposition portion 9 to fabricate a fluorocarbon region surrounded by a fluorocarbon film 6 and then the resist 5 acting as a mask is removed by, e.g., sulfuric acid and a hydrogen peroxide solution. At this time, the fluorocarbon film 6 deposited on the resist 5, together with the resist 5, is removed. As a result, the fluorocarbon film 6 remains over an inner surface of the tubular film deposition portion 9, thus enabling the fluorocarbon region to be formed (FIG. 18(c)).

Figure 18A:
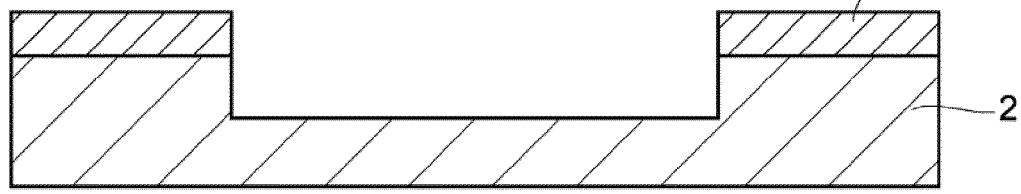
FIGS. 18 (a), (b), (c) and (d) are cross-sectional views illustrating partial fabricating processes of the single cell fixing microsystem according to the fourth embodiment of the present invention.
Figure 18B:
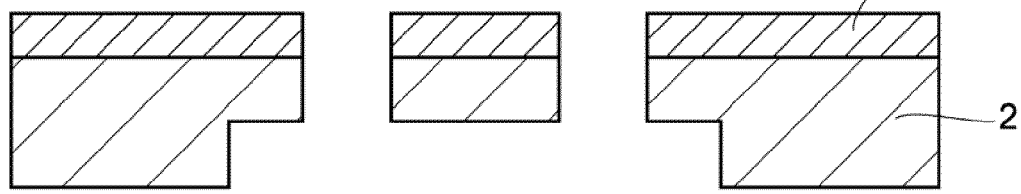
Figure 18C:
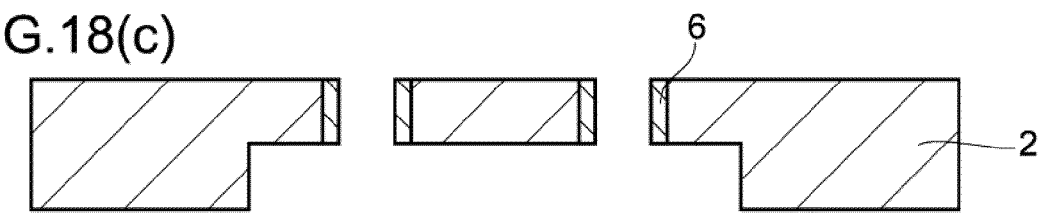
Figure 18D:
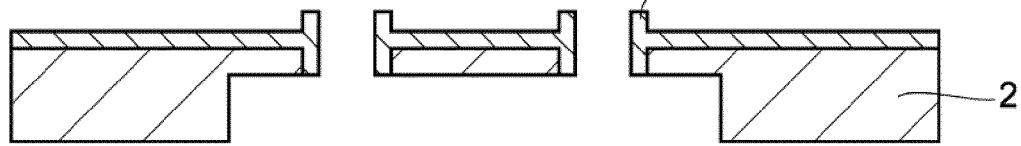

Further, in order to form the fluorocarbon microstructure 45 acting as a cell fixing protrusion, after having etched the whole of the other surface of the substrate 2, formed with the flow channel section 47 of the substrate 2 (not shown), a fluorocarbon film 6' is again formed over the surface of the substrate 2 (FIG. 18(d)).

Finally, the lid 43 for the flow channel comprising PDMS is provided on the substrate 2 (44) formed above, thus fabricating the single cell fixing microsystem 41.

The single cell fixing microsystem 41 thus structured can be used in the following fashion.

First, a petri dish 52 is filled with a cell suspension 53 containing a cell 51 intended to be fixed. The cell fixing protrusion comprising the fluorocarbon microstructure 45 of the single cell fixing microsystem 41 is immersed in the cell suspension 53. Then, air is sucked from the suction hole 42 of air to thereby decrease the pressure of the flow channel section 47 of the single cell fixing microsystem 41, fixing cells 52 one by one to the cell fixing protrusions comprising the fluorocarbon microstructure 45. Afterward, the single cell fixing microsystem 41 is taken up from the cell suspension 53. Then, by introducing the atmosphere from the suction hole 42 of air on a glass basal plate 54 or the like, the cell 51 can be withdrawn from the cell fixing protrusion comprising the fluorocarbon microstructure 45.

FIG. 20 shows fluorescent microscopic images taken during the time required to fix the cell 51 to the cell fixing protrusion 51 comprising the fluorocarbon microstructure 45. Here, a COS-1 (a kidney-derived cell of a Cercopithecus aethiops) was employed as the cell 51. It was learned from FIG. 20 that the cells 51 were fixed one by one to each cell fixing region. Various-size cells can be fixed to cell fixing sections by regulating a diameter of the cell fixing protrusion comprising the fluorocarbon microstructure 45.

As described above, the embodiments and examples of the present invention were set forth. The present invention, however, is not limited to the above embodiments and the above examples and therefore various modifications are possible.

The invention claimed is:

1. A process for producing a fluorocarbon microstructure comprising:
   a first processing step for forming, on a substrate, a film deposition portion with a given pattern made up of a depressed figure or a through-hole figure by etching said substrate,
   a fabricating step for forming a fluorocarbon film on an inner surface of said film deposition portion to fabricate a fluorocarbon region surrounded by said fluorocarbon film, and
   a second processing step for fabricating a fluorocarbon microstructure protruding from a processing surface of said substrate by etching a given region other than said fluorocarbon region on said substrate.

2. A process for producing a fluorocarbon microstructure according to claim 1, wherein a resist is patterned on said substrate to etch said substrate in said first processing step; the fluorocarbon film is formed on an inner surface of said film deposition portion and on said resist in said fabricating step; and a removing step is provided in which said resist and said fluorocarbon film on said resist are removed after said fabricating step.

3. A process for producing a fluorocarbon microstructure according to claim 1, wherein in said second processing step, a resist for said second processing step is patterned on said substrate and then a given region other than said fluorocarbon region on said substrate is etched.

4. A process for producing a fluorocarbon microstructure according to claim 1, wherein a silicon oxide film is already patterned on said substrate before said second processing step starts and then said substrate is etched with said silicon oxide film used as a mask in said second processing step.

5. A process for producing a fluorocarbon microstructure according to claim 2, wherein in said second processing step, a resist for said second processing step is patterned on said substrate and then a given region other than said fluorocarbon region on said substrate is etched.

* * * * *